(12) United States Patent
Perot et al.

(10) Patent No.: US 11,712,524 B2
(45) Date of Patent: Aug. 1, 2023

(54) MEDICAL INJECTION DEVICE FOR SUPPORTING A MEDICAL CONTAINER FILLED WITH A PHARMACEUTICAL COMPOSITION

(71) Applicant: Becton Dickinson France, Le Pont de Claix (FR)

(72) Inventors: Frédéric Perot, Saint Paul de Varces (FR); Gilles Bernede, Arbusigny (FR); Simon Gaschet, Annecy (FR)

(73) Assignee: Becton Dickinson France, Le Pont de Claix (FR)

( * ) Notice: Subject to any disclaimer, the term of this patent is extended or adjusted under 35 U.S.C. 154(b) by 406 days.

(21) Appl. No.: 16/969,946

(22) PCT Filed: Feb. 13, 2019

(86) PCT No.: PCT/EP2019/053481
§ 371 (c)(1),
(2) Date: Aug. 13, 2020

(87) PCT Pub. No.: WO2019/158547
PCT Pub. Date: Aug. 22, 2019

(65) Prior Publication Data
US 2020/0405971 A1   Dec. 31, 2020

(30) Foreign Application Priority Data

Feb. 16, 2018 (EP) .................................. 18305166

(51) Int. Cl.
*A61M 5/315* (2006.01)
*A61M 5/31* (2006.01)
*A61M 5/32* (2006.01)
*A61M 5/20* (2006.01)
*A61M 5/28* (2006.01)

(52) U.S. Cl.
CPC ...... *A61M 5/31581* (2013.01); *A61M 5/3129* (2013.01); *A61M 5/3202* (2013.01);
(Continued)

(58) Field of Classification Search
CPC ............ A61M 5/31581; A61M 5/3129; A61M 5/3202; A61M 5/2033; A61M 2205/583;
(Continued)

(56) References Cited

U.S. PATENT DOCUMENTS 6,302,868 B1    10/2001  Mohammad
9,132,236 B2 *   9/2015  Karlsson ................. A61M 5/32
(Continued)

FOREIGN PATENT DOCUMENTS

EP          2468328 A1    6/2012
EP          2654844 B1    3/2017
(Continued)

*Primary Examiner* — Bhisma Mehta
*Assistant Examiner* — Kathleen Paige Farrell
(74) *Attorney, Agent, or Firm* — The Webb Law Firm (57) ABSTRACT

A medical injection device for supporting a medical container comprising a barrel and a needle tip extending from a distal end of the barrel, comprising: safety shield, first ring configured to be coupled to the medical container and configured to be biased in a proximal direction relative to the safety shield from an injection position in which a needle tip extends out of the safety shield to a safety position in which the needle tip is covered by the safety shield, and second ring rotatably movable relative to the first ring between locking position wherein the second ring maintains the first ring in the injection position and an unlocking position wherein the second ring releases the first ring thereby allowing the first ring to be urged into the safety position.

15 Claims, 6 Drawing Sheets

(52) U.S. Cl.
CPC ............. *A61M 5/2033* (2013.01); *A61M 5/28* (2013.01); *A61M 5/3232* (2013.01); *A61M 5/3234* (2013.01); *A61M 5/3243* (2013.01); *A61M 5/3257* (2013.01); *A61M 2005/3239* (2013.01); *A61M 2205/583* (2013.01)

(58) Field of Classification Search
CPC ........ A61M 2005/3239; A61M 5/3257; A61M 5/28; A61M 5/3232; A61M 5/3234
See application file for complete search history.

(56) References Cited

U.S. PATENT DOCUMENTS

| | | | |
|---|---|---|---|
| 9,775,948 B2 | 10/2017 | Bechmann et al. | |
| 2010/0280460 A1* | 11/2010 | Markussen | A61M 5/322 604/195 |
| 2013/0281935 A1 | 10/2013 | Kemp et al. | |
| 2013/0331795 A1 | 12/2013 | Roberts et al. | |
| 2015/0190582 A1 | 7/2015 | Holmqvist | |
| 2015/0273160 A1* | 11/2015 | Olson | A61M 5/3257 |
| 2016/0001004 A1 | 1/2016 | Fourt et al. | |
| 2017/0021103 A1 | 1/2017 | Mosebach et al. | |
| 2017/0143911 A1* | 5/2017 | Roberts et al. | A61M 5/3234 |
| 2018/0001035 A1 | 1/2018 | Francavilla | |
| 2018/0110926 A1* | 4/2018 | Schrul | A61M 5/3159 |
| 2021/0138153 A1* | 5/2021 | Shanmugam | A61M 5/3257 |

FOREIGN PATENT DOCUMENTS

| | | |
|---|---|---|
| WO | 03045480 A1 | 6/2003 |
| WO | 2012093070 A1 | 7/2012 |
| WO | 2013034984 A2 | 3/2013 |
| WO | 2014159017 A1 | 10/2014 |
| WO | 2015140086 A1 | 9/2015 |

* cited by examiner

MEDICAL INJECTION DEVICE FOR SUPPORTING A MEDICAL CONTAINER FILLED WITH A PHARMACEUTICAL COMPOSITION

CROSS-REFERENCE TO RELATED APPLICATIONS

This application is the United States national phase of International Application No. PCT/EP2019/053481 filed Feb. 13, 2019, and claims priority to European Patent Application No. 18305166.3 filed Feb. 16, 2018, the disclosures of which are hereby incorporated by reference in their entirety.

TECHNICAL FIELD

The invention relates to a medical injection device for supporting a medical container filled with a pharmaceutical composition.

PRIOR ART

Prefilled injection devices are common containers to deliver drugs or vaccines to patients and include syringes, cartridges and autoinjectors or the like.

They usually comprise a sealing stopper in gliding engagement into a container. The container may be filled with a pharmaceutical composition in order to provide the practitioners with a ready-to-use injection device for patients.

A container has a substantially cylindrical shape, and comprises a proximal end able to be stoppered by a sealing stopper, a distal end wherein the pharmaceutical composition is expelled from the container, and a lateral wall extending between the proximal end and the distal end of the container. In practice, the sealing stopper is aimed at moving, upon the pressure exerted by a plunger rod, from a proximal end of the container body towards the distal end of the container body, thereby expelling the drug contained into the container body.

When compared to empty injection devices that are filled with a vial-stored pharmaceutical composition just prior to the injection to the patient's body, the use of prefilled injection devices leads to several advantages. In particular, by limiting the preparation prior to the injection, the prefilled injection devices provide a reduction of medical dosing errors, a minimized risk of microbial contamination and an enhanced convenience of use for the practitioners. Furthermore, such prefilled containers may encourage and simplify self-administration by the patients which allows reducing the cost of therapy and increasing the patient adherence. Finally, prefilled injection devices reduce loss of valuable pharmaceutical composition that usually occurs when a pharmaceutical composition is transferred from a vial to a non-prefilled injection device. This results in a greater number of possible injections for a given manufacturing batch of pharmaceutical product thus reducing buying and supply chain costs.

The injection can be a self-injection or can be performed by a user, such as a healthcare professional, to another person. In both cases, in order to perform the injection, the user positions the device in the vicinity of the injection area of the body, and pricks the skin with the needle. The user then pushes the plunger rod to carry out the injection of the composition.

At the end of the injection, the user withdraws the device from the skin of the body, which gives rise to a major drawback: the needle is left free and unprotected. This represents a high risk of accident for the user as well as for the patient or any person around who were to come into contact with the needle, and may lead to severe injuries.

BRIEF DESCRIPTION OF THE INVENTION

The invention aims to provide an injection device for injecting a composition contained in a medical container, such as a syringe, which prevents the user, the patient, or any person around the device, from coming into contact with the needle of the medical container after the injection has been carried out. In this way, the needle is in a safety position. The needle is not physically accessible, and the risk of accidental pricks or wounds generally caused by contact of the needle with a person close to the device is nullified. According to an embodiment, the injection device maintains the needle in said safety position thereby preventing any further injection from being carried out.

Another object of the invention is to provide an injection device that helps the patients to self-inject regularly with chronic drugs.

Another object of the invention is to provide an injection device that does not require any additional packaging. One object of the invention is a medical injection device to support a medical container comprising a barrel and a needle extending from a distal end of the barrel, comprising:
  a safety shield,
  a first ring coupled to the medical container and configured to be biased in a proximal direction relative to the safety shield from an injection position in which a needle tip extends out of the safety shield to a safety position in which the needle tip is covered by the safety shield, and
  a second ring rotatably movable relative to the first ring between a locking position wherein the second ring maintains the first ring in the injection position, and an unlocking position wherein the second ring releases the first ring thereby allowing the first ring to be urged into the safety position.

The movement of the first ring from the injection position to the safety position, when released by the second ring, causes the needle tip to be covered by the safety shield, thereby preventing the user or any person around the device from coming into contact with said needle tip. The safety shield thus acts as a physical protection that prevents injuries.

In this application, the "distal direction" is to be understood as meaning the direction of injection, with respect to the medical container the device of the invention is to be mounted on. The distal direction corresponds to the travel direction of the plunger rod during the injection, the pharmaceutical composition contained initially in the medical container being expelled from said medical container. The "proximal direction" is to be understood as meaning the opposite direction to said direction of injection.

According to other optional features of the device of the invention, taken separately or in combination when possible.

The medical injection device further comprises a plunger configured to move along an axis of the barrel in a distal direction to expel a pharmaceutical composition contained in the barrel from the needle, the plunger engaging the second ring so that an axial movement of the plunger in the distal direction causes the second ring to rotate from the locking position to the unlocking position. Hence, the plunger allows for both injecting the pharmaceutical composition and actuating the second ring.

The first ring is configured to support the medical container. In this manner, another element than the first ring is not required for supporting the medical container.

The medical injection device further comprises a protective ring configured to be mounted on a proximal end of the barrel and fixed to the first ring, for preventing the plunger from contacting said proximal end when moving towards the distal position. Thus, any risk of damaging the medical container is prevented. The protective ring may also contribute to achieve an optimal alignment of the plunger relative to the medical container.

The plunger and the second ring respectively comprise first and second cam members configured such that a translation of the first cam member in the distal direction causes a rotation of the second cam member.

The first and second cam members comprise respective sloped surfaces. Such sloped surfaces are quite simple to manufacture and simplify the overall structure of the device.

The first ring and the second ring are configured to be mutually connected by a bayonet-type mechanism when the second ring is in the locking position. This type of mechanism has a quite simple structure that is particularly convenient for achieving an optimal connection between a rotatable element, i.e. the second ring, and the first ring.

The plunger comprises a central rod configured to engage a stopper of the medical container and an outer sheath extending around the central rod configured to engage the second ring. Such structure is particularly adapted for the plunger to achieve the two functions described previously, both injecting the pharmaceutical composition and actuating the second ring.

The first ring comprises at least one snap feature that protrudes radially away from the axis, said snap feature being configured to engage a complementary snap feature provided in the safety shield when the first ring is in the safety position to maintain said safety position.

The first ring is advantageously configured to protrude axially from the safety shield at least partially when said first ring is in the safety position. Hence, the first ring acts as a visual indicator that informs the user that the first ring is in the safety position and the device is secured.

The first ring is biased preferably by a spring member.

A peripheral wall of the safety shield is provided with a window configured for allowing a user to visually assess a volume of a composition remaining in the barrel during the injection.

The outer sheath is configured to progressively close the window of the safety shield as the plunger moves distally.

The medical injection device further comprises a needle protective shield removably mounted on the distal end of the safety shield, the needle protective shield being configured to enclose the needle. Thus, before use of the device, any contact between the needle and a person around the device is prevented.

The medical device further comprises a plunger protective shield removably mounted on the proximal end of the safety shield, around the plunger, so as to prevent any actuation of said plunger.

The medical device further comprises tamper evidence means between the safety shield and at least one of the needle protective shield and the plunger protective shield.

BRIEF DESCRIPTION OF THE DRAWINGS

Further features and advantages of the invention will become apparent from the detailed description to follow, with reference to the appended drawings.

DETAILED DESCRIPTION OF EMBODIMENTS OF THE INVENTION

The invention proposes a medical injection device for supporting a medical container.

Prior to the injection, the medical container is filled with a composition intended to be injected, and stoppered with a stopper inserted therein. The stoppered medical container is then mounted on the device, and the injection of the composition can be carried out.

Figure 1:
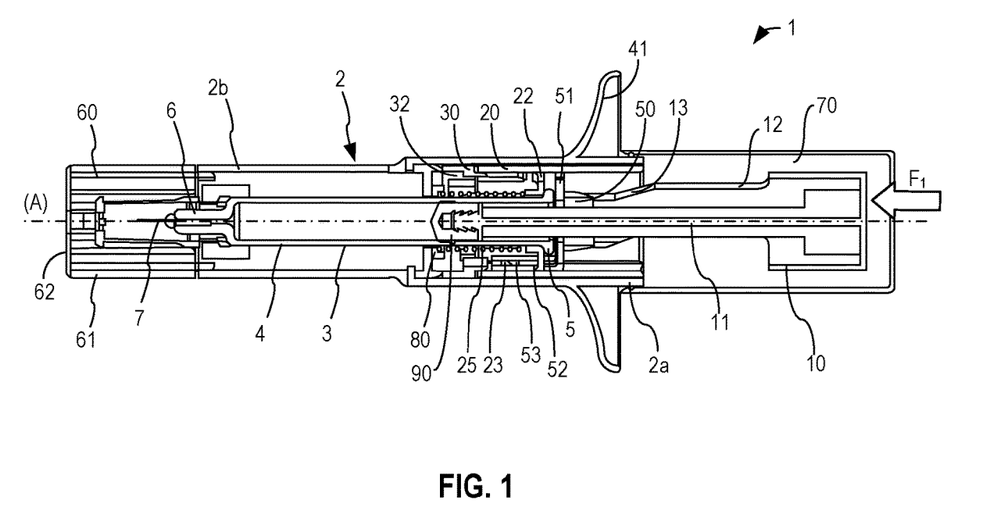
FIG. 1 is a side sectional view of an embodiment of the injection device of the invention, before use.
Figure 2:
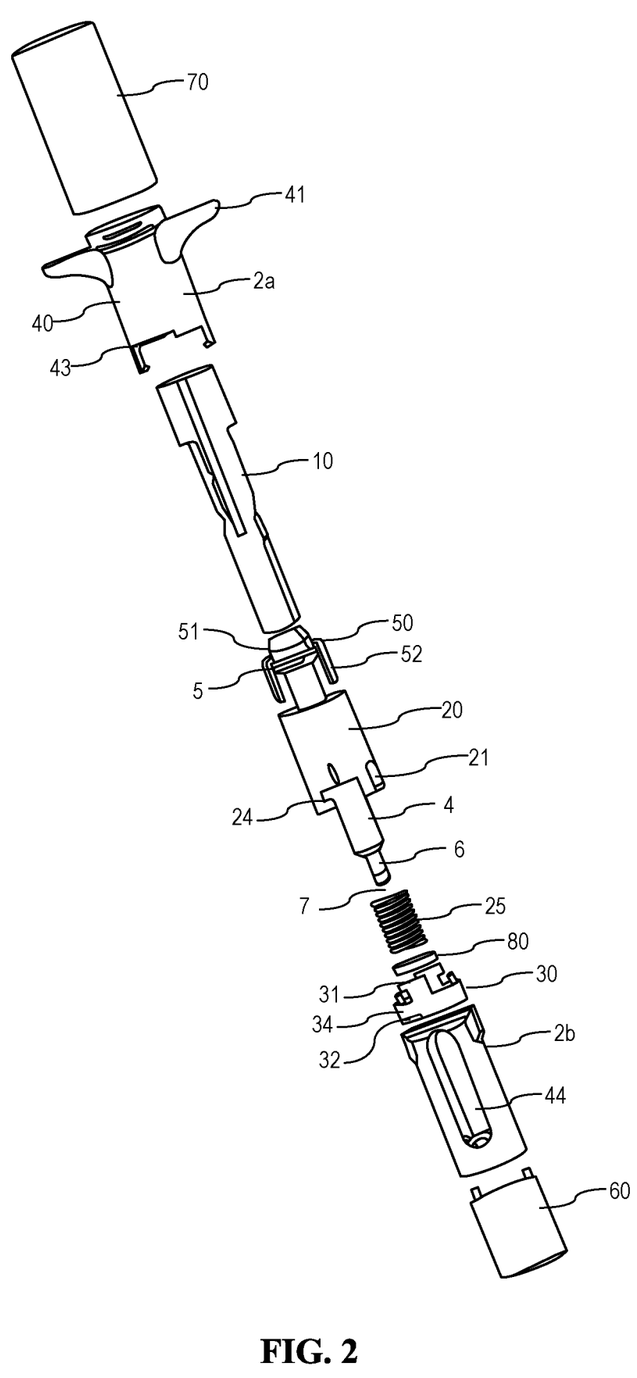
FIG. 2 is an exploded perspective view of the components of the injection device illustrated in FIG. 1.

A preferred embodiment of the injection device is represented in FIGS. 1 and 2.

According to this embodiment, the injection device 1 comprises a safety shield 2 extending along a longitudinal axis (A). The safety shield 2 preferably has a cylindrical shape. The safety shield 2 may be in two parts, a first part 2a and a second part 2b, adapted to be axially connected to each other thereby making the assembling of the device 1 easier, or in a single piece.

The safety shield 2 is adapted to be held by a user's hand. To that end, the safety shield is preferably provided with a grip surface 40 limited proximally by gripping means, such as arms 41 or a flange, that extend radially outwardly from the axis (A). Hence, when using the device 1, the user can easily grab the safety shield so that the palm of their hand contacts the grip surface 40 and the upper end of their hand abuts the gripping means, thus facilitating the handling of the device. Alternatively, the user can hold the grip surface 40 between their index finger and middle finger, both abutting the gripping means, as one would normally hold a standard syringe. The device is thus handheld and the dimensions and the weight of the device are advantageously adapted for this purpose. When the safety shield is in two parts, the grip surface is preferably provided on the first part 2a.

The safety shield is advantageously provided with a window 44 in its lateral wall, of an oblong shape in FIG. 2. The window allows the user to visually assess a volume of the composition remaining in the medical container during the injection. When the safety shield is in two parts, the window is preferably provided on the second part 2b.

The medical container 3 comprises a barrel 4 including a flange 5, and a distal end having a tip 6 and a needle 7 extending from thereon. The medical container 3 is preferably a prefilled syringe.

The device 1 further comprises a first ring 20 configured to support the medical container. The first ring 20 has preferably a cylindrical shape. The first ring 20 preferably extends around the medical container.

The first ring 20 is coupled to the medical container 3, preferably by a collar 22 configured to support the medical container. The collar 22 preferably extends radially inwardly from the inner wall of the first ring 20, around the barrel 4, and contacts the flange 5 of the medical container 3.

The first ring 20 is adapted to move in a proximal direction along the axis (A) relative to the safety shield 2, between an injection position and a safety position. The first ring 20 is preferably adapted to move into the safety shield 2. In other words, the first ring 20 is preferably at least partially inserted into the safety shield. The first ring 20 is biased in a proximal direction relative to the safety shield 2 by a spring member 25. In more details, the spring member 25 exerts a spring force in the proximal direction on the collar 22, thereby biasing said collar into contact with the flange 5 of the medical container. The spring member 25 is preferably mounted on a support piece 80 fixed to the safety shield 2.

The first ring 20 is provided with snap features 21 configured to be locked in complementary snap features 42 of the safety shield when the first ring is in safety position. To that purpose, as represented on the figures, the snap feature may be a flexible tab provided with a pin protruding radially outwardly. The complementary snap feature may be an opening in the safety shield, in which the flexible tab provided with the pin may be snapped.

According to the embodiment represented in FIGS. 1 and 2, the device may comprise a protective ring 50 having a base 51 and two arms 52 extending axially from thereon. The protective ring 50 is fixed to the first ring 20 by insertion of lugs 23 provided in the inner wall of the first ring in corresponding apertures 53 provided in the arms 52.

The collar 22 and the base 51 of the protective ring 50 border the flange 5 of the medical container positioned in-between, thereby supporting the medical container 3. The distance between the collar 22 and the base 51 is adapted to firmly maintain the flange 5, and may be adjusted to that end for example by adjusting the position of the lugs 23 along the inner wall of the first ring 20. Hence, the first ring 20 and the protective ring 50 constitute a support set that supports and maintains the medical container 3 in a fixed position relative to the first ring 20 and the protective ring 50. Having the first ring 20 and the protective ring 50 in two distinct pieces, as described previously, is mainly useful for making the assembling of the device easier. However, other arrangements are possible to achieve the support and maintaining of the medical container 3 without departing from the scope of the invention. For example, the protective ring 50 may be integral with the first ring 20, or a support set may be formed by two half-rings connected to each other along the axis (A) with the flange 5 of the medical container 3 in-between.

The device further comprises a second ring 30. The second ring 30 has preferably a cylindrical shape. The second ring 30 is preferably axially fixed to the safety shield 2. The second ring 30 is rotatably movable about the axis (A) relative to the first ring 20 between a locking position wherein the second ring 30 maintains the first ring 20 in the injection position and an unlocking position wherein the second ring 30 releases the first ring 20, thereby allowing the first ring 20 to be urged into the safety position. The second ring 30 is preferably partially inserted in the safety shield. The second ring 30 preferably extends around the medical container.

Figure 4A:
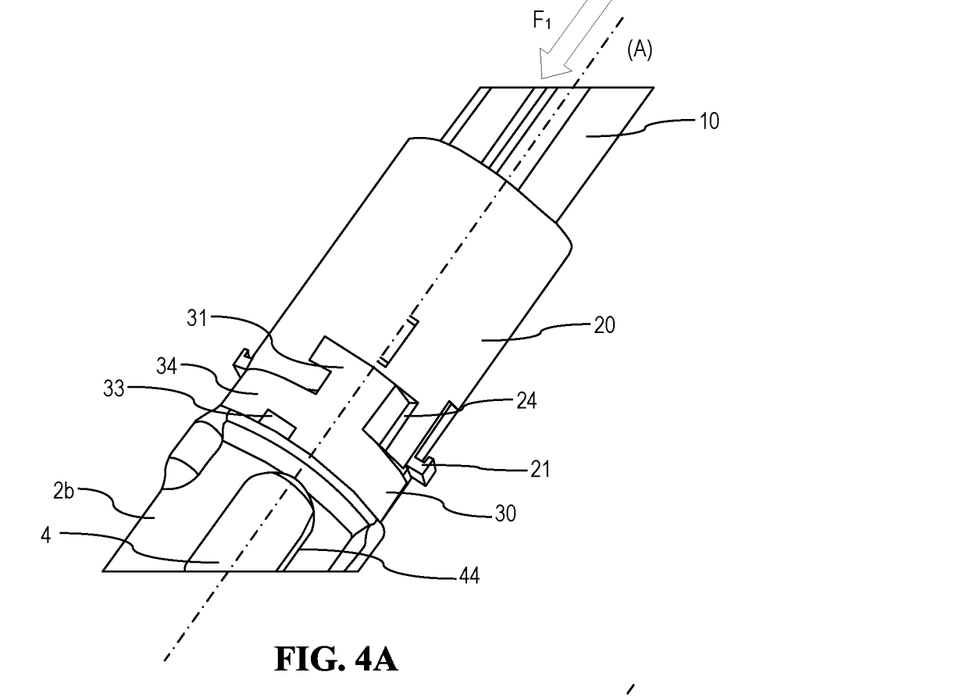
FIGS. 4A and 4B are perspective views of the device respectively before and after the injection, wherein the second ring rotates from the locking position to the unlocking position.
Figure 4B:
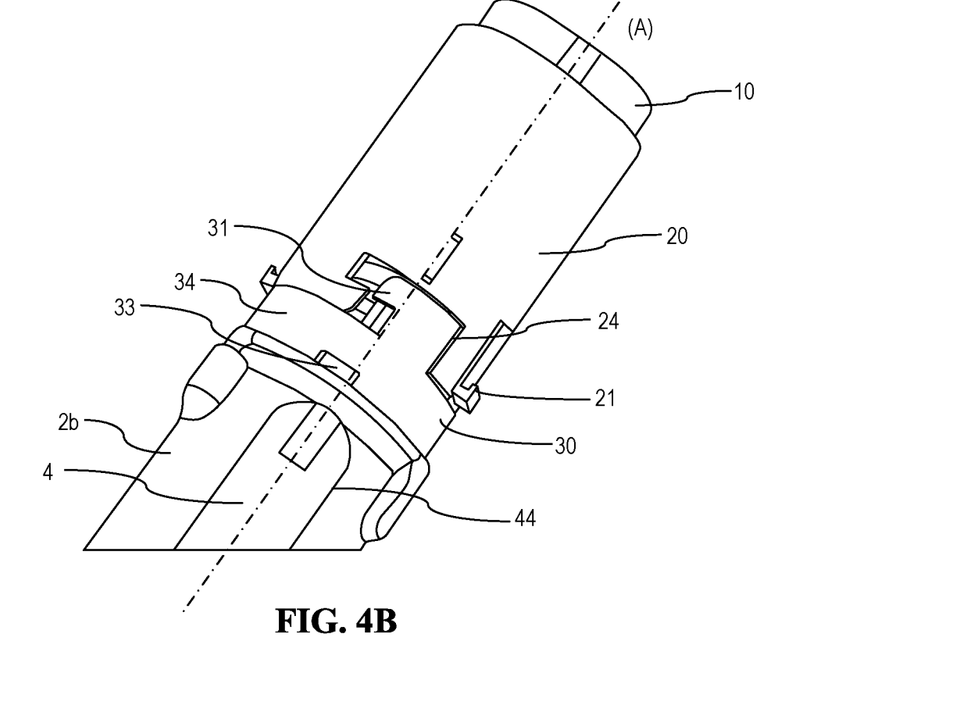

The maintaining and releasing of the first ring 20 by the second ring 30 is achieved by connection means, an embodiment of which is illustrated in FIG. 2 and mainly in FIGS. 4A and 4B, in the form of a bayonet-type mechanism. According to this embodiment, the first ring 20 preferably comprises a first L-shape element 24 while the second ring 30 comprises a second L-shape element 31. The second L-shape element 31 is inverted with respect to the first L-shape element 24. In locking position the two L-shape elements are interlocked together, so that the first ring 20 is not allowed to axially move with respect to the second ring 30. When the second ring 30 rotates with respect to the first ring 20, the second L-shape element 31 is disengaged from the first L-shape element 24 so that the first ring 20 is free to axially move with respect to the second ring 30. Of course, other connection means instead of the bayonet-type mechanism are possible provided that they achieve a similar function.

The second ring 30 also preferably comprises a visual indicator 33 that can be seen though a slot 43 of the lateral wall of the safety shield 2. When the second ring 30 is in locking position, the visual indicator 33 is not aligned with the slot 43 so that the visual indicator 33 is invisible. When the second ring 30 is in unlocking position, the visual indicator 33 is aligned with the slot 43 of the safety shield so it can be seen through the slot 43.

The device 1 further comprises a plunger 10 translationally movable inside the safety shield 2 along the axis (A) in the distal direction.

The plunger 10 comprises a central rod 11. The central rod is configured to slide into the medical container 3 in a distal direction and to push the stopper 90 contained therein to expel the composition contained in a medical container 3 from the needle 7.

The plunger also preferably comprises an outer sheath 12 extended around and at a distance from the central rod 11. The outer sheath 12 is preferably inserted in the first ring 20 and in the second ring 30. The outer sheath 12 is preferably configured to surround the medical container. The outer sheath 12, is preferably configured to cause the second ring 30 to rotate from the locking position to the unlocking position when the plunger moves in distal direction.

To that end, the outer sheath 12 of the plunger 10 and the second ring 30 preferably comprise a first cam member 13 and a second cam member 32 respectively, advantageously in the form of corresponding slopes. The first and second cam members 13, 32 are configured to cooperate with each other, such that a translation of the first cam member 13 in the distal direction due to a corresponding translation of the outer sheath 12 causes a rotation of the second cam member 32 and thereby a rotation of the second ring 30 about the axis (A), from the locking position to the unlocking position.

The outer sheath 12 is preferably configured to close progressively the window 44 of the safety shield when the plunger moves distally. The outer sheath 12 is preferably configured to completely close the window 44 at the end of injection.

Before use of the device, a needle protective shield 60 may optionally be removably mounted on the distal end of the safety shield 2 so as to enclose the needle 7. The needle protective shield 60 is preferably mounted on the tip 6 of the medical container. When mounted, the lateral wall 61 of the needle protective shield 60 extends around the tip 6 and protrudes distally from the tip to a distal wall 62.

A plunger protective shield 70 may optionally be removably mounted on the proximal end of the safety shield 2, around the plunger 10, so as to prevent any actuation of the plunger 10. The plunger protective shield 70 preferably presents a cylindrical shape. The plunger protective shield

70 is preferably fixed to the safety shield so that it can be removed by a user. For example, the plunger protective shield 70 may be clipped on the safety shield 2.

The needle protective shield 60, the plunger protective shield 70 and the safety shield 2 are preferably rigid.

Before use, the needle protective shield 60, the plunger protective shield 70 and the safety shield 2 preferably form a packaging enclosing the medical container so that no further packaging is required.

Tamper evidence means may be provided between the needle protective shield 60 and the safety shield and/or between the plunger protective shield 70 and the safety shield 2.

In the following, the functioning of the device will be detailed in reference to the embodiment of the device described above. It has to be known that other embodiments of the device would result in a similar functioning, notwithstanding their structural differences.

FIG. 1 shows the injection device 1 before use.

The plunger 10 is in a proximal position. The first ring 20 is in the injection position. In this position, the tip 7 of the medical container 3 extends out of the distal end of the safety shield 2.

The second ring 30 is in the locking position. The second L-shape element 31 of the second ring 30 engages the first L-shape element 24 of the first ring 20 so that the first ring 20 is not allowed to move axially, thereby maintaining the first ring in the injection position, as shown more particularly in FIG. 4A.

When present, the needle protective shield 60 encloses the needle 7, and the plunger protective shield 70 prevents any actuation of the plunger 10.

To carry out the injection, the needle protective shield 60 and plunger protective shield 70 are removed from the safety shield 2.

The user pricks the patient's skin with the needle and pushes the plunger 10 in the distal direction according to the arrow $F_1$.

Figure 3A:
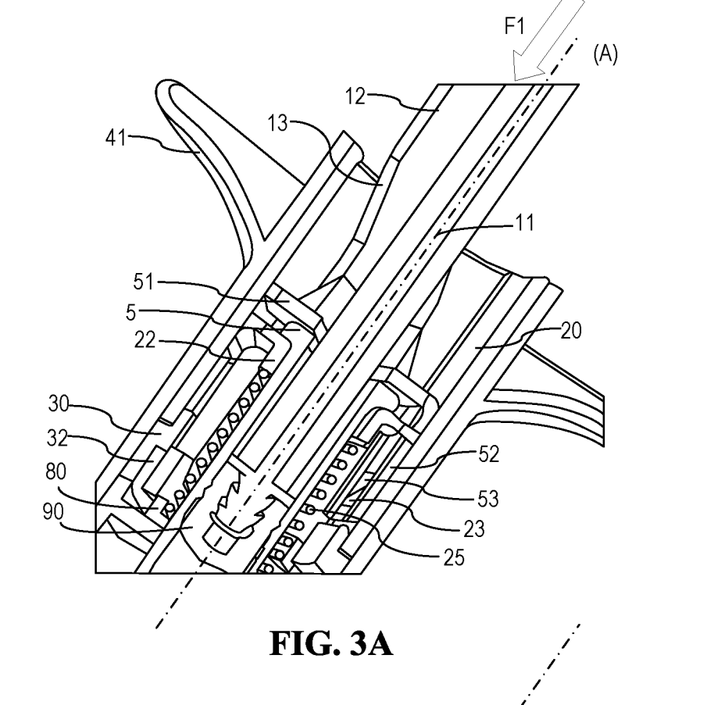
FIGS. 3A and 3B are perspective sectional views of the device respectively before and after the injection, showing the movement of the plunger in the distal direction.
Figure 3B:
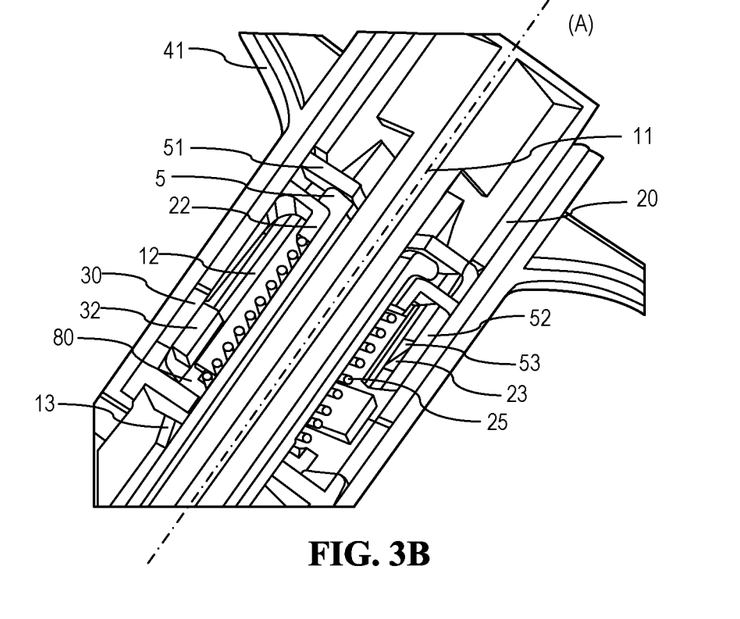

In reference to FIGS. 3A and 3B, when the plunger 10 moves in the distal direction, the central rod 11 slides in the medical container 3 and pushes the stopper 90, thereby expelling the composition contained in the barrel 4 from the needle 7.

Figure 5:
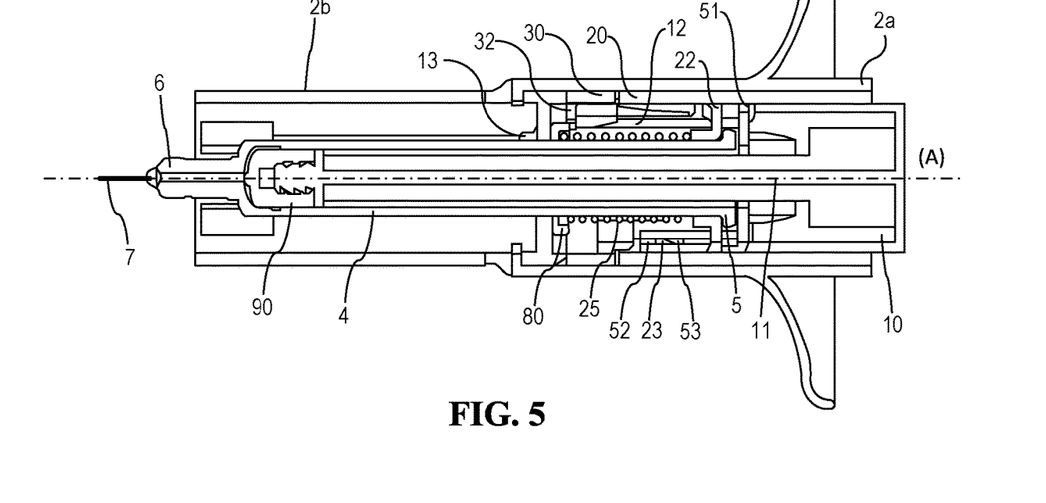
FIG. 5 is a side sectional view of the device after injection of the composition contained in a medical container.

At the end of the injection, when all the composition contained in the container 3 has been injected, the stopper 90 abuts the tip 6, and the plunger 10 cannot be pushed further distally. The device is then as illustrated in FIG. 5.

At the end of injection, the outer sheath 12 slides towards the second ring 30. The surfaces of the slopes 13, 32 of the outer sheath 12 and the second ring 30 contact and slide onto one another, which causes the second ring 30 to rotate about the axis (A), from the locking position to the unlocking position.

In reference to FIGS. 4A and 4B, the rotation of the second ring 30 causes the second L-shape element 31 to disengage the first L-shape element 24 of the first ring 20, thereby releasing the first ring 20. The user may visually note the rotation of the second ring 30 via a corresponding displacement of the visual indicator 33 with respect to the slot 43 of the safety shield 2.

Figure 6:
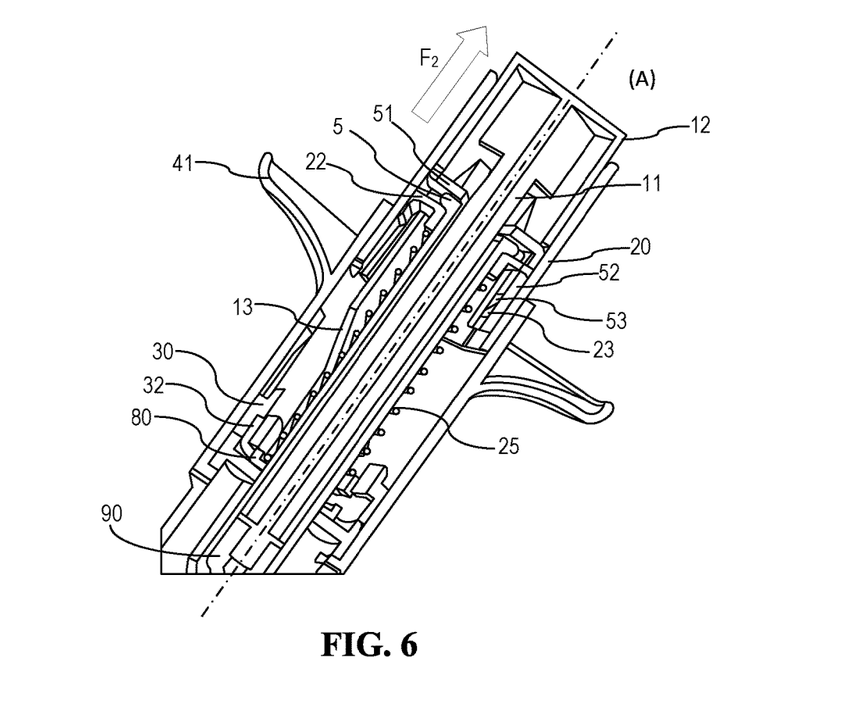
FIG. 6 is a side sectional view of the device, wherein the first ring is urged into the safety position.
Figure 7:
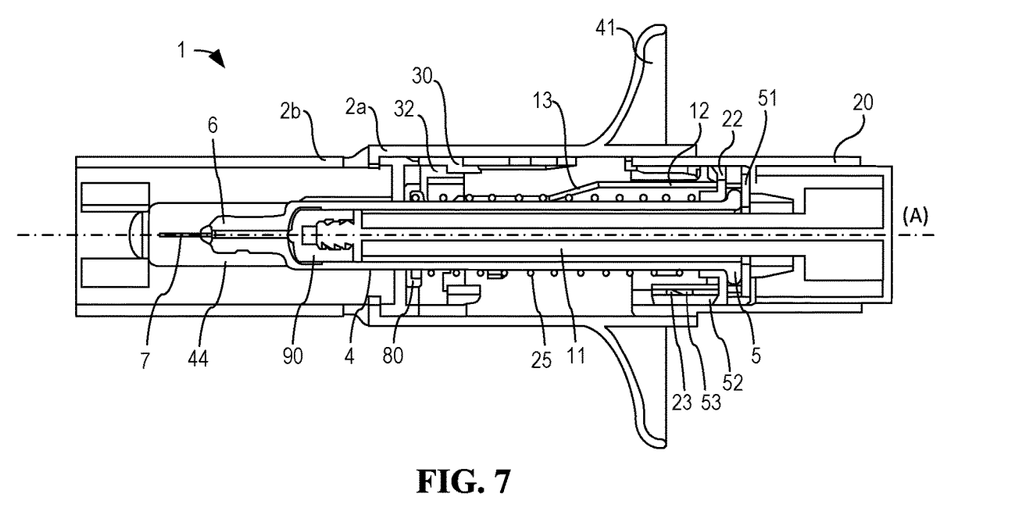
FIG. 7 is a side sectional view of the device after use, the first ring being maintained in the safety position.

In reference to FIG. 6, the releasing of the first ring 20 by the second ring 30 causes the first ring 20, and the medical container mounted thereon, to be urged by the spring member 25 in the proximal direction, according to the arrow $F_2$, into the safety position. As the collar 22 abuts the flange 5 of the medical container 3, the medical container is moved along with the first ring 20. And as the stopper 90 abuts the distal end of the barrel 4, the plunger 10 is moved along with the medical container 3. The device is then in a secured configuration, as illustrated in FIG. 7.

In this secured configuration, the safety shield 2 extends around the needle 7 and protrudes distally from the needle 7. The needle 7 is thus completely covered by the safety shield 2, thereby preventing any contact of the needle 7 with the user or any person in the vicinity of the device and any possible resulting injury. The device is advantageously configured so that, when the first ring 20 is in the safety position, the user may see the needle 7 through the window 44.

Figure 8:
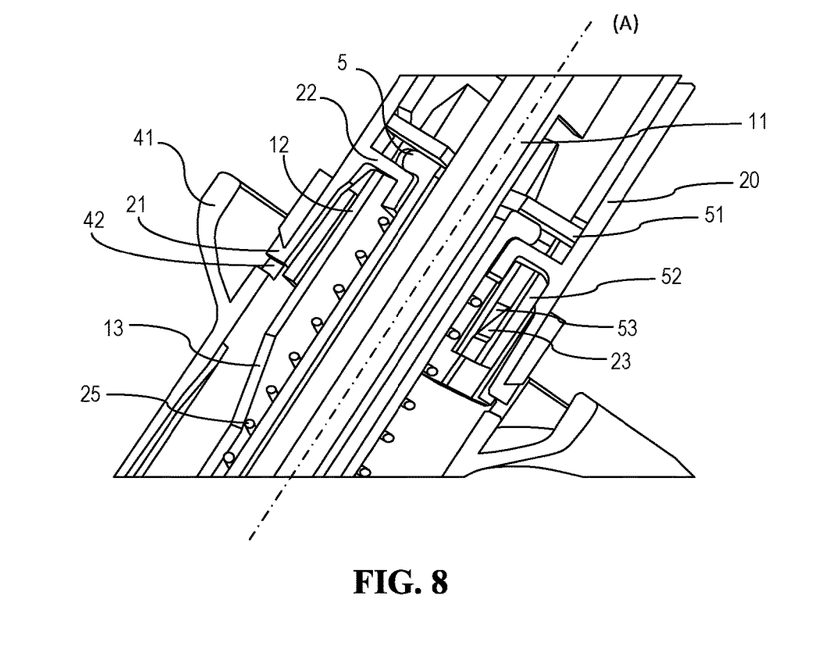
FIG. 8 is a close-up sectional view of the device of FIG. 7, centered on the first ring.

The snap features 21, in frictional engagement with the inner surface of the safety shield 2 until then, are now locked in the complementary snap features 42 of the safety shield 2 as illustrated in FIG. 8, thereby blocking the first ring 20 in the safety position. Advantageously, the first ring 20 protrudes proximally from the first part 2a of the safety shield 2, so as to serve as a visual indicator allowing the user to know that the device is secured.

The medical container 3 is prevented from moving both in a distal direction and in a proximal direction, due to the abutment of the flange 5 with the collar 22 and the protective ring 50 respectively.

The plunger 10 is prevented from moving in a distal direction due to the abutment of the central rod 11 and stopper 90 with the tip 6 of the medical container 3.

Therefore, when the device is secured, the first ring 20, and the medical container 3 cannot be moved relative to the safety shield 2, and in particular, cannot be disassembled from said safety shield, making the device unable to be further used.

The invention claimed is:

1. A medical injection device for supporting a medical container comprising a barrel and a needle tip extending from a distal end of the barrel, comprising:
   a safety shield;
   a first ring configured to be coupled to the medical container and move into the safety shield, wherein the first ring is configured to be biased in a proximal direction relative to the safety shield from an injection position in which a needle tip extends out of the safety shield to a safety position in which the needle tip is covered by the safety shield; and
   a second ring rotatably movable relative to the first ring between a locking position wherein the second ring maintains the first ring in the injection position, and an unlocking position wherein the second ring releases the first ring thereby allowing the first ring to be urged into the safety position.

2. The medical injection device of claim 1, further comprising a plunger configured to move along an axis of the barrel in a distal direction to expel a pharmaceutical composition contained in the barrel from a needle, the plunger engaging the second ring so that an axial movement of the plunger in the distal direction causes the second ring to rotate from the locking position to the unlocking position.

3. The medical injection device of claim 2, wherein the plunger and the second ring respectively comprise first and second cam members configured such that a translation of the first cam member in the distal direction causes a rotation of the second cam member.

4. The medical injection device of claim 3, wherein the first and second cam members comprise respective sloped surfaces.

5. The medical injection device of claim 2, wherein the plunger comprises a central rod configured to engage a stopper of the medical container and an outer sheath extending around the central rod configured to engage the second ring.

6. The medical device of claim 2, further comprising a plunger protective shield removably mounted on a proximal end of the safety shield, around the plunger, so as to prevent any actuation of said plunger.

7. The medical device of claim 6, further comprising:
a needle protective shield removably mounted on a distal end of the safety shield, the needle protective shield being configured to enclose the needle.

8. The medical injection device of claim 1, wherein the first ring is configured to support the medical container.

9. The medical injection device of claim 1, wherein the first ring and the second ring are configured to be mutually connected by a bayonet-type mechanism when the second ring is in the locking position.

10. The medical injection device of claim 1, wherein the first ring comprises at least one snap feature that protrudes radially away from an axis, said at least one snap feature being configured to engage a complementary snap feature provided in the safety shield when the first ring is in the safety position to maintain said safety position.

11. The medical injection device of claim 1, wherein the first ring is configured to protrude axially from the safety shield at least partially when said first ring is in the safety position.

12. The medical injection device of claim 1, wherein the first ring is biased by a spring member.

13. The medical injection device of claim 1, wherein a peripheral wall of the safety shield is provided with a window configured for allowing a user to visually assess a volume of a composition remaining in the barrel during injection.

14. The medical injection device of claim 13, further comprising a plunger, wherein the plunger comprises a central rod configured to engage a stopper of the medical container and an outer sheath extending around the central rod configured to engage the second ring, the outer sheath being configured to progressively close the window of the safety shield as the plunger moves distally.

15. The medical injection device of claim 1, further comprising a needle protective shield removably mounted on a distal end of the safety shield, the needle protective shield being configured to enclose a needle.

* * * * *